United States Patent
Black et al.

(10) Patent No.: US 6,342,499 B1
(45) Date of Patent: Jan. 29, 2002

(54) PARASITIC AND SAPROPHAGOUS MITE CONTROL IN BENEFICIAL INSECTS

(75) Inventors: Bruce Christian Black, Yardley, PA (US); William R. Baumbach, Hopewel; Michael P. Beluch, Belle Mead, both of NJ (US)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/352,507

(22) Filed: Jul. 12, 1999

Related U.S. Application Data

(60) Provisional application No. 60/092,755, filed on Jul. 14, 1998.

(51) Int. Cl.[7] .................... A01N 43/54; A01N 31/00; A01N 33/00; A01N 35/00; A01N 37/00
(52) U.S. Cl. .................. 514/256; 514/247; 514/248; 514/257; 514/258; 514/259; 514/269; 514/274; 514/506; 514/532; 514/579; 514/580; 514/675; 514/682; 514/706; 514/715; 514/740; 514/741; 514/742
(58) Field of Search .................. 514/256–259, 514/269, 274, 359, 360, 406, 407, 506, 532, 579, 580, 679, 682, 706, 715, 740, 741, 742, 247, 248

(56) References Cited

U.S. PATENT DOCUMENTS

| 4,950,688 A | 8/1990 | Okada et al. |
| 5,707,995 A | 1/1998 | Munro et al. |

FOREIGN PATENT DOCUMENTS

| EP | 0972770 A | 1/2000 | |
| WO | WO 94/02470 | 2/1994 | ......... C07D/239/52 |
| WO | WO 9747193 A | 12/1997 | |
| WO | WO 98/12184 | 3/1998 | ......... C07D/239/52 |

OTHER PUBLICATIONS

"Fenpyroximate. Orchard Acaricide.", (Phytoma. Def. Veg., No. 450, pp. 42–44 (1993)), Accession No. 93–83914, STN/CAS, CROPU, Abstract.*

Mayer et al., "Susceptibility of four bee species (Hymenoptera: Apoidea) to field weathered insecticide residues", (J. Entomol. Soc. of British Columbia, vol. 94, No. 0, pp. 27–30 (Dec. 1997)), Acc. No. 1998: 216522, STN/CAS, BIOSIS, Abstract.*

Canson et al., "Fenazaquin. Apple Acaricide.", (Phytoma Def. Veg., No. 453, pp. 41–42 (1993)), Accession No. 93–86784, STN/CAS, CROPU,Abstract.*

C. Tomlin, "The Pesticide Manual," 11th Ed., British Crop Protection Council, 1997, compound No. 315 (fenpyroximate).

* cited by examiner

*Primary Examiner*—Jose' G. Dees
*Assistant Examiner*—Frank Choi
(74) *Attorney, Agent, or Firm*—Barbara V. Maurer

(57) ABSTRACT

The present invention provides a method to control parasitic and saprophagous mites on beneficial insects such as honeybees via the application of a parasiticidally or saprophagouscidally effective amount of a mitochondrial electron transport inhibitor or a pyrimidine compound of formula I.

(I)

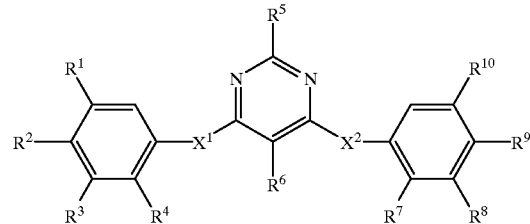

17 Claims, No Drawings

PARASITIC AND SAPROPHAGOUS MITE CONTROL IN BENEFICIAL INSECTS

This application claims priority from copending provisional application(s) Ser. No. 60/092,755 filed on Jul. 14, 1998.

BACKGROUND OF THE INVENTION

Beneficial insects, particularly the honeybee, are susceptible to infestation and damage caused by parasitic mites. Recently, a plague of parasitic mites has significantly decreased the honeybee population. Honeybees are important for crop pollination and aid in fruit formation and size and enhance crop yield. Measures of control of the parasitic mite populations are few and unpredictable.

Parasitic and saprophagous mites are a serious threat for many cultured insects used for scientific research and for production of insect hosts for biocontrol agents. Saprophagous mites such as Histiostoma sp. and parasitic mites such as Proctolaelaps sp. may cause significant loss of Drosophila stock cultures commonly used for scientific research. Decreased fitness of mite-infested Drosophila cultures may complicate the interpretation of genetic crosses. Moreover, various parasitic and saprophagous mite species greatly interfere with the rearing of roaches, house flies, beetles, crickets, white flies, thrips, aphids, and lepidoptera. The inability to effectively control mite infestations using conventional methods may result in the loss of valuable insect cultures. Further, production of extremely large insect colonies such as those used for silkworm production, for bait, for sterile insect release programs, (i.e. the Mediterranean Fruit Fly, Gypsy Moth, Screwworm Fly) and the like, are vulnerable to mite infestation and the damage and loss caused thereby. Also, the propagation of biocontrol agents such as Diptera (Spalagiodae and Tachinidae) for the biocontrol of flies (Diptera) and Hymenoptera (Trichogrammatidae, Ichneumonidae, Braconidae, Apidae, Eulophidae, Chalcididae, and Spalangiadae) for the biocontrol of Lepidoptea, Coleoptera, Diptera and Homoptera require healthy insect hosts. The propagation of viral biocontrol agents (baculoviruses, granuloviruses, and emtomapox viruses) may also be seriously affected by the presence of mites. Currently there are no effective means to rid insect colonies of these dangerous parasitic and saprophagous mites.

Therefore, new methods are needed to provide selective control of parasitic and saprophagous mites on beneficial insects and protection of said insects from infestation and damage caused by parasitic and saprophagous mites with little or no concommitant harm to the beneficial host insect.

SUMMARY OF THE INVENTION

The present invention provides a method for the protection of beneficial insects from infestation and damage caused by parasitic or saprophagous mites which comprises applying to said insects, their breeding ground or habitat a parasiticidally effective amount of a mitochondrial electron transport inhibitor or a formula I pyrimidine compound

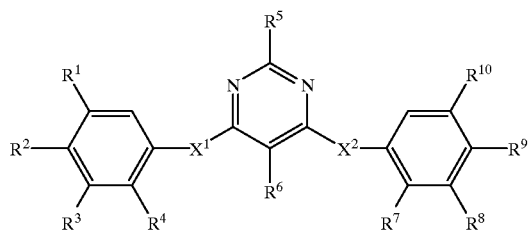

(I)

wherein
 $X^1$ and $X^2$ are each independently O, $S(O)_n$, CO, $CH_2$, or NR;
 n is 0, 1, or 2;
 R is hydrogen or $C_1$–$C_6$alkyl;
 $R^1$ and $R^{10}$ are each independently hydrogen or halogen;
 $R^2$ and $R^9$ are each independently hydrogen, halogen, CN, $NO_2$, $C_1$–$C_6$haloalkyl, $C_1$–$C_6$alkoxy, $C_1$–$C_6$alkylthio, $NR^{11}R^{12}$, $C_1$–$C_6$alkoxycarbonyl or $C_1$–$C_6$alkyl optionally substituted with one or more $C_1$–$C_4$alkoxy or $C_1$–$C_4$ haloalkoxy groups;
 $R^{11}$ and $R^{12}$ are each independently hydrogen or $C_1$–$C_6$alkyl;
 $R^3$ and $R^8$ are each independently hydrogen, chlorine, CN, $NO_2$, $C_1$–$C_6$haloalkyl, $C_2$–$C_6$haloalkenyl, $C_2$–$C_6$haloalkynyl, $C_1$–$C_6$haloalkoxy, $C_1$–$C_6$haloalkylthio, $C_1$–$C_6$haloalkylsulfinyl, $C_1$–$C_6$haloalkylsulfonyl, $C_1$–$C_6$haloalkoxycarbonyl, or $C_1$–$C_6$alkyl optionally substituted with one or more $C_1$–$C_4$alkoxy groups;
 $R^4$ and $R^7$ are each independently hydrogen, halogen, $C_1$–$C_6$alkyl or $C_1$–$C_6$alkoxy;
 $R^5$ is hydrogen, halogen, CN, $C_1$–$C_6$alkyl, $C_1$–$C_6$haloalkyl, $C_1$–$C_6$alkoxy, $C_1$–$C_6$alkylthio, $C_1$–$C_6$alkylsulfinyl or phenyl; and
 $R^6$ is hydrogen, or when $R_5$ is hydrogen, $C_1$–$C_6$alkyl.

Preferred formula I compounds are those wherein either each of the two phenyl rings is unsubstituted or at least one of $R^3$ and $R^8$ is other than hydrogen.

As used herein the term "parasiticidally effective" is defined to be less than the effective $LD_{50}$ for the beneficial insect (dosage rate required to obtain 50% mortality of healthy uninfected insects), but sufficient to control or suppress the infestation of parasitic mites and/or saprophagous mites.

The invention further provides a method for the selective control of parasitic mites in the presence of beneficial insects.

DETAILED DESCRIPTION OF THE INVENTION

Beneficial insects such as Apidae, for example, Apinae (honeybees), Bombinae (bumblebees) and Euglossinae (orchid bees) are susceptible to attack and infestation by parasitic mites, particularly mites such as Varroa jacobsoni (Varroa mites), Acarapis woodi (tracheal mites) and Tropilaelaps clareae. These parasites feed on the insect's blood via the trachea (tracheal mites), via the cuticle from the brood or adult (Varroa mites) or the larvae (T. clareae) causing physical deformation, deterioration and death. Further, parasitic mites may either transmit or "trigger" viruses in honeybees and other beneficial insects. Currently, a plague of parasitic mites has caused significant global concern over the present and future populations of essential agronomically important insects such as the honeybee.

Further, saprophagous mites such as Histiostoma sp. and parasitic mites such as Proctolaelaps sp. cause significant loss of Drosophila stock cultures commonly used for scientific research. Various parasitic and saprophagous mite species greatly interfere with the rearing of roaches, houseflies, beetles, crickets, white flies, thrips, aphids, and lepidoptera. Mite infestation control on beneficial insects using conventional miticidal methods currently results in the loss of valuable insect cultures, decreased propagation of biocontrol agents which require healthy insect hosts, and decreased propagation of viral biocontrol agents.

Effective miticides that discriminate between the insect host and parasitic or saprophagous mites have heretofore not been identified. The performance of current miticides on beneficial insects yields unpredictable results and incomplete control.

Surprisingly, it has now been found that a mitochondrial electron transport inhibitor or a formula I pyrimidine compound may be used to effectively control parasitic and saprophagous mites in the presence of beneficial insects and for the protection of said insects from the infestation and damage caused by parasitic and saprophagous mites. Advantageously, the method of the invention may be used to control both the Varroa mite and the tracheal mite in the presence of beneficial insects, particularly honeybees, with little or no significant harmful effect to the insect host. Further, the method of the invention may be used to control parasitic and saprophagous mite populations in insect colonies committed to scientific research and the production of insect biocontrol agents.

Mitochondrial electron transport inhibitors, hereinafter designated METI, such as pyrazole carboxamides, quinones, thioureas, quinazolines, pyridazinones, pyrimidinamines, and the like all interfere with mitochondrial transport. It has now been found that these particular inhibitors are useful for the selective control of parasitic and saprophagous mites in the presence of beneficial insects.

Among the METI preferred for use in the method of invention are fenpyroximate, acequinocyl, diafenthiuron, fenazaquin, pyridaben and pyrimidifen.

Many pyrimidine compounds, including the formula I pyrimidine compounds, methods for their preparation and the insecticidal and acaricidal uses thereof are described in U.S. Pat. No. 5,707,995 and WO 98/12184. Among the broad class of pyrimidine compounds described, surprisingly, it has now been found that those particular pyrimidine compounds of formula I are useful for the protection of beneficial insects from infestation and damage caused by parasitic mites.

Preferred pyrimidine compounds of formula I useful in the method of the invention are those compounds wherein $X^1$ and $X^2$ are each O or NR;

$R^1$, $R^3$, $R^8$ and $R^{10}$ are each independently hydrogen or trifluoromethyl, with the proviso that at least one of $R^1$, $R^3$, $R^8$, and $R^{10}$ must be trifluoromethyl;

$R^2$ and $R^9$ are each independently hydrogen, chlorine or fluorine; and $R^4$, $R^5$, $R^6$, and $R^7$ are hydrogen.

More preferred formula I pyrimidine compounds useful in the inventive method are 4-[(4-chloro-α,α,α-trifluoro-m-tolyl)oxy]-6-[(α,α,α, 4-tetrafluoro-m-tolyl)oxy]-pyrimidine; 4-(α,α, α,4-tetrafluoro-N-methyl-m-toluidino)-6-[(α,α,α, 4-tetrafluoro-m-tolyl)oxy]pyrimidine; and 4,6 bis [(α,α,α, 4-tetrafluoro-m-tolyl)oxy]pyrimidine.

In actual practice a METI or formula I pyrimidine compound may be applied to the beneficial insect breeding ground or habitat such as a beehive, nest, brood chamber, or the like using a conventional delivery system. For example, formula I pyrimidines or METI may be applied to mite-infested beneficial insect colonies or research laboratory insect cultures in the form of diet incorporation, or by insertion into the colony or culture of an impregnated strip, or by utilization of available standard delivery systems. Effective amounts of the METI or formula I pyrimidine compound will vary according to the miticidal sensitivity of the beneficial insect species, the degree of mite infestation, the insect population density, habitat construction, weather conditions, the timing of the beneficial insect life cycle, and the like. In general, parasiticidally effective amounts may be about 0.001–10 μg per insect.

For a more clear understanding of the invention, the following examples are set forth below. These examples are merely illustrative and are not understood to limit the scope or underlying principles of the invention in any way. Indeed, various modifications of the invention, in addition to those shown and described herein, will become apparent to those skilled in the art from the following examples and the foregoing description. Such modifications are also intended to fall within the scope of the appended claims.

EXAMPLE 1

Evaluation of the Efficacy of Formula I Pyrimidines Against *Varroa jacobsoni* Parasites In this evaluation, honeybees (*Apis mellifera*) taken from hives which are 70% infested with *Varroa jacobsoni* (Varroa mites) are chilled to immobilize the bees. A 1 μl droplet of an acetone solution of test compound is applied to the dorsal abdomen of each bee. Control bees receive a 1 μl droplet of acetone. A total of 50–52 bees are treated for each dose rate tested. Treatment dose rates are based upon the $LD_{50}$ (dose rate required to obtain 50% mortality of healthy uninfected bees) of each test compound and are set at 10% of the $LD_{50}$ and subsequent 10-fold dilutions thereof. The treated bees are placed in an incubator at 31° C. in the dark and fed 50% sugar water ad libitum for 5 days. After incubation, the bees are examined for mortality and mite infestation. The results are shown in Table I below.

TABLE I

| Test Compound[1] | Dose (μg/bee) | % Mortality Bees | % Mortality Parasites |
|---|---|---|---|
| A | 0.08 | 21 | 75 |
| A | 0.8 | 13 | 100 |
| A | 8.0 | 21 | 92 |
| B | 0.002 | 16 | 6 |
| B | 0.02 | 14 | 36 |
| B | 0.2 | 10 | 88 |
| Control | 0.0 | 14 | 0 |

[1]Test Compound A = 4-(α,α,α,4-tetrafluoro-N-methyl-m-toluidino)-6-[(α,α,α,4-tetrafluoro-m-tolyl)oxy]pyrimidine
[1]Test Compound B = 4,6 bis[(α,α,α 4-tetrafluoro-m-tolyl)oxy]pyrimidine

EXAMPLE 2

Evaluation of the Efficacy of Formula I Pyrimidines Against *Varroa jacobsoni* Parasites Using essentially the same procedure described in Example 1, but employing honeybees which are 90% infected with *Varroa jacobsoni*, the following results are obtained and shown in Table II below.

TABLE II

| Test Compound[1] | Dose (μg/bee) | % Mortality Bees | Mites |
|---|---|---|---|
| C | 0.01 | 13 | 8 |
|   | 0.10 | 12 | 80 |
|   | 1.00 | 16 | 91 |
| Control | 0.0 | 10 | 14 |

[1]Test Compound C = 4-(α,α,α,4-tetrafluoro-N-methyl-m-toluidino)-6-[(α,α,α,4-tetrafluoro-m-tolyl)oxy]pyrimidine

EXAMPLE 3
Evaluation of the Efficacy of Formula I Pyrimidines Against *Acarapis woodi* Parasites In this evaluation, honeybees (*Apis mellifera*) which are infested with *Acarapis woodi* (trachea mites) are dissected to remove the infested tracheae. Glass microscope slides are dipped into acetone solutions of test compound (500 ppm) and the acetone is allowed to evaporate. Infested tracheae are placed directly on the treated slides. The mites are removed from the tracheae by dissection and forced to walk across the treated area. The elapsed time is recorded for 100% mortality, i.e. no movement is observed upon agitation. The results are shown in Table III below.

TABLE III

| Test Compound[1] | Rep. 1 No. mites | Rep. 1 Time[2] | Rep. 2 No. mites | Rep. 2 Time[2] | Rep. 3 No. mites | Rep. 3 Time[2] |
|---|---|---|---|---|---|---|
| C | 4 | 16 | 3 | 16 | 4 | 15 |
| Control | 6 | >35 | 4 | >25 | — | — |

[1]Test Compound C = 4-[(4-chloro-α,α,α-trifluoro-m-tolyl)oxy]-6-[(α,α,α,4-tetrafluoro-m-tolyl)-oxy]pyrimidine
[2]Time required in minutes to achieve 100% mortality.

EXAMPLE 4
Evaluation of the Efficacy of METI Against *Varroa jacobsoni* Parasites Honeybees (*Apis mellifera*) taken from hives which are 70% infested with *Varroa jacobsoni* are chilled to immobilize the bees. A 1 μl droplet of an acetone solution of test compound is applied to the dorsal abdomen of each bee; control bees receive a 1 μl droplet of acetone. A total of 50–52 bees are treated for each dose rate tested. The treated bees are placed in an incubator at 31° C. in the dark and fed 50% sugar water ad libitum for 5 days. After incubation, the bees are examined for mortality and mite infestation. The results are shown in Table IV below.

TABLE IV

| Test Compound | Dose (μg/bee) | % Mortality Bees | Parasites |
|---|---|---|---|
| Fenpyroximate | 0.003 | 13 | 7 |
|   | 0.03 | 10 | 30 |
|   | 0.3 | 24 | 100 |
| Fenazaquin | 0.012 | 18 | 19 |
|   | 0.12 | 14 | 27 |
|   | 1.2 | 18 | 87 |

TABLE IV-continued

| Test Compound | Dose (μg/bee) | % Mortality Bees | Parasites |
|---|---|---|---|
| Pyridaben | 0.001 | 12 | 14 |
|   | 0.01 | 10 | 0 |
|   | 0.1 | 20 | 100 |
| Acequinocyl | 0.1 | 15 | 12 |
|   | 1.0 | 10 | 0 |
|   | 10.0 | 42 | 83 |
| Control | 0.0 | 14 | 0 |

EXAMPLE 5

Evaluation of the Efficacy of Formula I Pyrimidines Against Proctolaelaps Sp. and Histiostoma Sp. Mites Paper towel strips (2×7 cm) are dipped into an acetone solution of test compound and allowed to dry. Control paper towel strips are dipped into acetone and allowed to dry. Treated strips are placed in 2.5×9.5 cm culture vials containing a standard cornmeal-molasses-agar diet, such that the strips are inserted about 1 cm into the diet. Five pairs of heavily infested, newly emerged *Drosophila melanogaster* are placed into the test vials and incubated at 25° C. After 5 days, the adult flies are evaluated for % mortality and are removed rom each test vial. After 15 days, the mites [Proctoloaelaps sp.(Proct) and Histiostoma sp.(Hist)] and insect larva/pupa are evaluated for mortality and recorded as a percent of expected progeny as determined by the untreated control. At 14 days approximately 200–500 Histiostoma sp. mites (Hist) and approximately 50 Proctolaelaps sp. mites (Proct) are present in the untreated controls.

TABLE V

| Test Compound[1] | Dose (ppm) | Drosophila Adults | Drosophila larvae | Mites Proct | Mites Hist |
|---|---|---|---|---|---|
| C | 100 | 100 | 73 | 100 | 100 |
| C | 50 | 20 | 53 | 100 | 100 |
| C | 10 | 15 | 0 | 40 | 90 |
| Control | 0 | 10 | 0 | 0 | 0 |

[1]Test Compound C = 4-[(4-chloro-α,α,α-trifluoro-m-tolyl)oxy]-6-](α,α,α,4-tetrafluoro-m-tolyl)-oxy]pyrimidine

What is claimed is:

1. A method for the protection of an Apidae or cultured insect colonies committed to scientific research or the production of insect biocontrol agents from infestation and damage caused by parasitic or saprophagous mites which comprises applying to said Apidae or cultured insect, their breeding ground or habitat a miticidally effective amount of a formula I pyrimidine compound

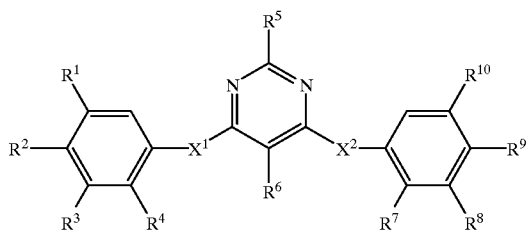

(I)

wherein
- $X^1$ and $X^2$ are each independently O, $S(O)_n$, CO, $CH_2$, or NR;
- n is 0, 1, or 2;
- R is hydrogen or $C_1$–$C_6$alkyl;
- $R^1$ and $R^{10}$ are each independently hydrogen or halogen;
- $R^2$ and $R^9$ are each independently hydrogen, halogen, CN, $NO_2$, $C_1$–$C_6$haloalkyl, $C_1$–$C_6$alkoxy, $C_1$–$C_6$alkylthio, $NR^{11}R^{12}$, $C_1$–$C_6$alkoxycarbonyl or $C_1$–$C_6$alkyl optionally substituted with one or more $C_1$–$C_4$alkoxy or $C_1$–$C_4$haloalkoxy groups;
- $R^{11}$ and $R^{12}$ are each independently hydrogen or $C_1$–$C_6$alkyl;
- $R^3$ and $R^8$ are each independently hydrogen, chlorine, CN, $NO_2$, $C_1$–$C_6$haloalkyl, $C_2$–$C_6$haloalkenyl, $C_2$–$C_6$haloalkyl, $C_1$–$C_6$haloalkoxy, $C_1$–$C_6$haloalkylthio, $C_1$–$C_6$haloalkylsulfinyl, $C_1$–$C_6$haloalkylsulfonyl, $C_1$–$C_6$haloalkoxycarbonyl, or $C_1$–$C_6$alkyl optionally substituted with one or more $C_1$–$C_4$alkoxy groups;
- $R^4$ and $R^7$ are each independently hydrogen, halogen, $C_1$–$C_6$alkyl or $C_1$–$C_6$alkoxy;
- $R^5$ is hydrogen, halogen, CN, $C_1$–$C_6$alkyl, $C_1$–$C_6$haloalkyl, $C_1$–$C_6$alkoxy, $C_1$–$C_6$alkylthio, $C_1$–$C_6$alkylsulfinyl or phenyl; and
- $R^6$ is hydrogen or, when $R^5$ is hydrogen, $C_1$–$C_6$alkyl, wherein said miticidally effective amount controls the parasitic or saprophagous mites and causes little or no significant harmful effect to the Apidae or cultured insect.

2. The method according to claim 1 wherein the formula I compound has either each of the two phenyl rings is unsubstituted or at least one of $R^3$ and $R^8$ being other than hydrogen.

3. The method according to claim 2 having the formula I pyrimidine compound wherein $X^1$ and $X^2$ are each O or NR;
- $R^1$, $R^3$, $R^8$ and $R^{10}$ are each independently hydrogen or trifluoromethyl;
- $R^2$ and $R^9$ are each independently hydrogen, chlorine or fluorine; and
- $R^4$, $R^5$, $R^6$, and $R^7$ are hydrogen.

4. The method according to claim 3 wherein the formula I pyrimidine compound is selected from the group consisting of 4-[(4-chloro-α,α,α-trifluoro-m-tolyl)oxy]-6-[(α,α,α,4-tetrafluoro-m-tolyl)oxy]pyrimidine; 4-(α,α,α,4-tetrafluoro-N-methyl-m-toluidino)-6-[(α,α,α, 4-tetrafluoro-m-tolyl)oxy]pyrimidine; and 4,6 bis[(α,α,α 4-tetrafluoro-m-tolyl)oxy]pyrimidine.

5. The method according to claim 1 wherein the cultured insect is a Drosophila.

6. The method according to claim 1 wherein the parasitic mites are selected from the group consisting of *Varroa jacobsoni, Acarapis woodi* and *Tropilaelaps clareae*.

7. The method according to claim 1 wherein the Apidae are *Apis meillifera*.

8. The method according to claim 7 wherein the parasitic mites are *Varroa jacobsoni* or *Acarapis woodi*.

9. A method for the control of parasitic or saprophagous mites in the presence of an Apidae or cultured insect colonies committed to scientific research or the production of insect biocontrol agents which comprises contacting said mites, their breeding grounds or habitat in the presence of said Apidae or cultured insect with a miticidally effective amount of a formula I pyrimidine compound (I)

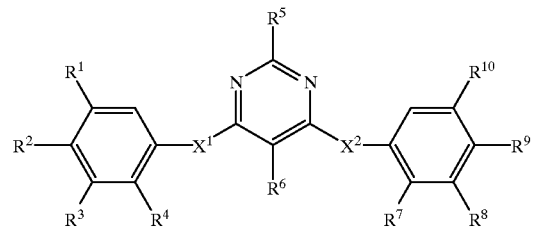

wherein
- $X^1$ and $X^2$ are each independently O, $S(O)_n$, CO, $CH_2$, or NR;
- n is 0, 1, or 2;
- R is hydrogen or $C_1$–$C_6$ alkyl;
- $R^1$ and $R^{10}$ are each independently hydrogen or halogen;
- $R^2$ and $R^9$ are each independently hydrogen, halogen, CN, $NO_2$, $C_1$–$C_6$haloalkyl, $C_1$–$C_6$alkoxy, $C_1$–$C_6$alkylthio, $NR^{11}R^{12}$, $C_1$–$C_6$alkoxycarbonyl or $C_1$–$C_6$alkyl optionally substituted with one or more $C_1$–$C_4$alkoxy or $C_1$–$C_4$haloalkoxy groups;
- $R^{11}$ and $R^{12}$ are each independently hydrogen or $C_1$–$C_6$alkyl;
- $R^3$ and $R^8$ are each independently hydrogen, chlorine, CN, $NO_2$, $C_1$–$C_6$haloalkyl, $C_2$–$C_6$haloalkenyl, $C_2$–$C_6$haloalkynl, $C_1$–$C_6$haloalkoxy, $C_1$–$C_6$haloalkylthio, $C_1$–$C_6$haloalkylsulfinyl, $C_1$–$C_6$haloalkylsulfonyl, $C_2$–$C_6$haloalkoxycarbonyl, or $C_1$–$C_6$alkyl optionally substituted with one or more $C_1$–$C_4$alkoxy groups;
- $R^4$ and $R^7$ are each independently hydrogen, halogen, $C_1$–$C_6$alkyl or $C_1$–$C_6$alkoxy;
- $R^5$ is hydrogen, halogen, CN, $C_1$–$C_6$ alkyl, $C_1$–$C_6$ haloalkyl, $C_1$–$C_6$alkoxy, $C_1$–$C_6$alkylthio, $C_1$–$C_6$alkylsulfinyl or phenyl; and
- $R^6$ is hydrogen or, when $R^5$ is hydrogen, $C_1$–$C_6$ alkyl, wherein said miticidally effective amount controls the parasitic or saprophagous mites and causes little or no significant harmful effect to the Apidae or cultured insect.

10. The method according to claim 9 wherein the formula I compound has either each of the two phenyl rings is unsubstituted or at least one of $R^3$ and $R^8$ being other than hydrogen.

11. The method according to claim 10 having the formula I pyrimidine compound wherein $X^1$ and $x^2$ are each O or NR;
- $R^1$, $R^3$, $R^8$ and $R^{10}$ are each independently hydrogen or trifluoromethyl with the proviso that at least one of $R^1$, $R^3$, $R^8$ and $R^{10}$ must be trifluoromethyl;

$R^2$ and $R^9$ are each independently hydrogen, chlorine or fluorine; and $R^4$, $R^5$, $R^6$, and $R^7$ are hydrogen.

12. The method according to claim 11 wherein the formula I pyrimidine compound is selected from the group consisting of 4-[(4-chloro-α,α,α-trifluoro-m-tolyl)oxy]-6-[(α,α,α, 4-tetrafluoro-m-tolyl)oxy]pyrimidine; 4-(α,α,α,4-tetrafluoro-N-methyl-m-toluidino)-6-[(α,α,α,4-tetrafluoro-m-tolyl)oxy]pyrimidine; and 4,6 bis[(α,α,α 4-tetrafluoro-m-tolyl)oxy]pyrimidine.

13. The method according to claim 9 wherein the Apidae are Apis mellifera.

14. The method according to claim 13 wherein the parasitic mites are selected from the group consisting of *Varroa jacobsoni, Acarapis woodi* and *Tropiladaelaps clareae*.

15. The method according to claim 9 wherein the cultured insect is a Drosophila.

16. A method for the protection of an Apidae from infestation and damage caused by parasitic or saprophagous mites which comprises applying to said Apidae, their breeding ground or habitat a miticidally effective amount of a mitochondrial electron transport inhibitor selected from the group consisting of acequinocyl, diafenthiuron, fenazaquin, pyridaben and pyrimidifen, wherein said miticidally effective amount controls the parasitic or saprophagous mites and causes little or no significant harmful effect to the Apidae.

17. A method for the control of parasitic or saprophagous mites in the presence of an Apidae which comprises contacting said mites, their breeding grounds or habitat in the presence of an Apidae with a miticidally effective amount of a mitochondrial electron transport inhibitor selected from the group consisting of acequinocyl, diafenthiuron, fenazaquin, pyridaben and pyrimidifen, wherein said miticidally effective amount controls the parasitic or saprophagous mites and causes little or no significant harmful effect to the Apidae.

\* \* \* \* \*